United States Patent [19]

Lesher et al.

[11] Patent Number: 4,473,571

[45] Date of Patent: Sep. 25, 1984

[54] 8-SUBSTITUTED-2-(4-PYRIDINYL)-9H-PURIN-6-AMINES AND THEIR CARDIOTONIC USE

[75] Inventors: George Y. Lesher, Schodack; Baldev Singh, East Greenbush, both of N.Y.

[73] Assignee: Sterling Drug Inc., New York, N.Y.

[21] Appl. No.: 458,297

[22] Filed: Jan. 17, 1983

[51] Int. Cl.³ .................... A61K 31/52; C07D 473/34
[52] U.S. Cl. .................................. 424/253; 544/277; 544/276
[58] Field of Search ................. 544/277, 276; 424/253

[56] References Cited

U.S. PATENT DOCUMENTS 3,041,340  6/1962  Bullock et al. ...................... 260/252

OTHER PUBLICATIONS

Taylor et al., [J. Am. Chem. Soc. 81, 2442–8, (1959)].
Baddiley et al., [J. Chem. Soc. 1943, pp. 386–387].

Primary Examiner—Nicholas S. Rizzo
Attorney, Agent, or Firm—Robert K. Bair; B. Woodrow Wyatt; Paul E. Dupont

[57] ABSTRACT

8-Q-2-PY-9H-purin-6-amines (II), salts thereof, their preparation and cardiotonic use are shown, where PY is 4-pyridinyl or 4-pyridinyl having one or two lower-alkyl substituents, and Q is methyl, ethyl, 1-methylethyl, 1,1-dimethylethyl, methylthio and ethylthio. Also shown as intermediates for the compounds where Q is methylthio or ethylthio are the corresponding 6-amino-2-PY-9H-purin-8-thiols.

8 Claims, No Drawings

8-SUBSTITUTED-2-(4-PYRIDINYL)-9H-PURIN-6-AMINES AND THEIR CARDIOTONIC USE

BACKGROUND OF THE INVENTION (a) Field of the Invention

This invention relates to selected 8-(substituted)-2-(4-pyridinyl)-9H-purin-6-amines, their preparation and cardiotonic use, and to intermediates therefor.

(b) Description of the Prior Art

Taylor et al [J. Am. Chem. Soc. 81, 2442-8 (1959)] show, inter alia, the preparation of 2-(3-pyridinyl)-9H-purin-6-amine by heating the nicotinamidine salt of isonitrosomalonitrile in formamide to produce 4,6-diamino-5-nitroso-2-(3-pyridinyl)pyrimidine and heating the reaction mixture containing said 5-nitroso compound and formamide with a mixture of formic acid and sodium dithionite dihydrate to produce said 2-(3-pyridinyl)-9H-purin-6-amine, for which no use is indicated.

Baddiley et al [J. Chem. Soc. 1943, pp. 386-7] show the catalytic hydrogenation of 4,6-diamino-5-phenyl-azopyrimidine in ethanol using Raney nickel as catalyst to produce 4,5,6-triaminopyrimidine.

Bullock et al [U.S. Pat. No. 3,041,340, issued June 26, 1962] show, inter alia, N-(4-, 3- and 2-pyridinyl)-9H-purin-6-amines as vegetable growth stimulants.

SUMMARY OF THE INVENTION

In a composition of matter aspect, the invention resides in 8-Q-2-PY-9H-purin-6-amines or acid-addition salts thereof, useful as cardiotonic agents or intermediates, where Q and PY are defined hereinbelow.

A composition aspect of the invention resides in a cardiotonic composition for increasing cardiac contractility in a patient, said composition comprising a pharmaceutically acceptable carrier and, as the active ingredient thereof, a cardiotonically effective amount of an 8-Q-2-PY-9H-purin-6-amine or pharmaceutically acceptable acid-addition salt thereof.

In a method aspect, the invention resides in a method for increasing cardiac contractility in a patient requiring such treatment which comprises the administration of a medicament comprising a pharmaceutically acceptable carrier and, as the active component thereof, a cardiotonically effective amount of an 8-Q-2-PY-9H-purin-6-amine or pharmaceutically acceptable acid-addition salt thereof.

The invention in a process aspect comprises reacting 2-PY-4,5,6-pyrimidinetriamine with an alkanoylating agent providing QCO to produce 8-Q-2-PY-9H-purin-6-amine.

In another composition of matter aspect, the invention resides in 2-PY-4,5,6-pyrimidinetriamine or acid-addition salt thereof.

DETAILED DESCRIPTION INCLUSIVE OF PREFERRED EMBODIMENTS

In a composition of matter aspect the invention resides in a 8-Q-2-PY-9H-purin-6-amine having formula I

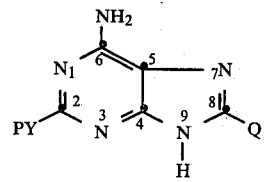

where Q is methyl, ethyl, 1-methylethyl, 1,1-dimethylethyl, mercapto, methylthio or ethylthio, and Py is 4-pyridinyl or 4-pyridinyl having one or two lower-alkyl substituents, or acid-addition salts thereof. The compounds of formula I where Q is mercapto are useful as intermediates for preparing the corresponding compounds of formula I where Q is methylthio or ethylthio. The other compounds of formula I, that is, those where Q is methyl, ethyl, 1-methylethyl, 1,1-dimethylethyl, methylthio or ethylthio, are useful as cardiotonic agents, as determined by standard pharmacological evaluation procedures. Preferred embodiments are those of formula I where Py is 4-pyridinyl and Q is 1-methylethyl, methyl or ethylthio.

A composition aspect of the invention resides in a cardiotonic composition for increasing cardiac contractility, said composition comprising a pharmaceutically acceptable carrier and, as the active component thereof, a cardiotonically effective amount of 8-Q-2-PY-9H-purin-6-amine of formula I or pharmaceutically acceptable acid-addition salt thereof, where Q is methyl, ethyl, 1-methylethyl, 1,1-dimethylethyl, methylthio or ethylthio. Preferred embodiments are those having as active components the compounds of formula I where PY is 4-pyridinyl and Q is 1-methylethyl, methyl or ethylthio.

A method aspect of the invention resides in the method for increasing cardiac contractility in a patient requiring such treatment which comprises administering orally or parenterally in a solid or liquid dosage form to such patient a medicament comprising a pharmaceutically acceptable carrier and, as the active component thereof, a cardiotonically effective amount of the compound of formula I where Q is methyl, ethyl, 1-methylethyl, 1,1-dimethylethyl, methylthio or ethylthio or pharmaceutically acceptable acid-addition salt thereof. Preferred embodiments are those using as active components the compounds of formula I wherein PY is 4-pyridinyl and Q is 1-methylethyl, methyl or ethylthio.

In a process aspect the invention resides in the process which comprises reacting 2-PY-4,5,6-pyrimidinetriamine with an alkanoylating agent providing QCO to produce 8-Q-2-PY-9H-purin-6-amine where Q is methyl, ethyl, 1-methylethyl or 1,1-dimethylethyl and PY is 4-pyridinyl or 4-pyridinyl having one or two lower-alkyl substituents. Preferred embodiments of this process aspect are those which produce said compounds where PY is 4-pyridinyl and Q is 1-methylethyl or methyl.

Another composition of matter aspect of the invention resides in 2-PY-4,5,6-pyrimidinetriamine having formula II

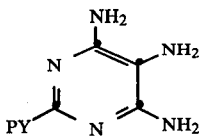

or acid-addition salt thereof, where PY is 4-pyridinyl or 4-pyridinyl having one or two lower-alkyl substituents. A preferred embodiment is 2-(4-pyridinyl)-4,5,6-pyrimidinetriamine.

The term "lower-alkyl" as used herein, e.g., as a substituent for PY in formulas I and II, means alkyl radicals having from one to four carbon atoms which can be arranged as straight or branched chains, illustrated by methyl, ethyl, n-propyl, 1-methylethyl, n-butyl, 1-methylpropyl, 1,1-dimethylethyl or 3-ethylpropyl.

Illustrative of PY in formulas I and II where Py is 4-pyridinyl having one or two lower-alkyl substituents are the following: 2-methyl-4-pyridinyl, 2,6-dimethyl-4-pyridinyl, 3-methyl-4-pyridinyl, 2,3-dimethyl-4-pyridinyl, 2,6-dimethyl-4-pyridinyl, 2-ethyl-4-pyridinyl, 2-(1-methylethyl)-4-pyridinyl, 2-n-butyl-4-pyridinyl, 2,6-diethyl-4-pyridinyl, 2,6-di-(1-methylethyl)-4-pyridinyl, and the like.

The compounds of formulas I and II are useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts, especially those of the cardiotonically active compounds of formula I, include preferably those which produce, when combined with the free base, pharmaceutically acceptable salts, that is, salts whose anions are relatively innocuous to the animal organism in pharmaceutical doses of the salts, so that the beneficial cardiotonic properties inherent in the free base (II) are not vitiated by side effects ascribable to the anions. In practicing the invention, it is convenient to use the free base form and the methanesulfonate or hydrochloride salt; however, appropriate pharmaceutically acceptable salts within the scope of the invention are those derived from other mineral acids such as hydrobromic acid, sulfuric acid, phosphoric acid and sulfamic acid; and organic acids such as acetic acid, citric acid, lactic acid, tartaric acid, ethanesulfonic acid, benzenesulfonic acid, p-toluenesulfonic acid, cyclohexylsulfamic acid, quinic acid, and the like, giving the hydrobromide, sulfate, phosphate, sulfamate, acetate, citrate, lactate, tartrate, ethanesulfonate, benzenesulfonate, cyclohexylsulfamate and quinate, respectively.

The acid-addition salts of said basic compounds are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically acceptable salts of said basic compounds are preferred, all acid-addition salts are within the scope of the invention. All acid-addition salts are useful as sources of the free base form even if the particular salt per se is desired only as an intermediate product as for example when the salt is formed only for purposes of purification or identification, or when it is used as an intermediate in preparing a pharmaceutically acceptable salt by ion exchange procedures.

The molecular structures of the compounds of formulas I and II were assigned on the basis of evidence provided by infrared, nuclear magnetic resonance and mass spectra, and by the correspondence of calculated and found values for the elementary analysis.

The manner of making and using the instant invention will now be generally described so as to enable a person skilled in the art of pharmaceutical chemistry to make and use the same as follows.

The preparation of 8-Q-2-PY-9H-purin-6-amine where Q is methyl, ethyl, 1-methylethyl or 1,1-dimethylethyl by reacting 2-PY-4,5,6-pyrimidinetriamine of formula II with an alkanoylating agent providing alkanoyl, i.e., Q—C(=O)—, can be carried out using various alkanoylating agents, namely, alkanoic acids, alkanoic acid anhydrides or halides, or, for compounds of formula I where Q is methyl or ethyl, dimethylacetamide dimethyl acetal or dimethylpropionamide dimethyl acetal, respectively, or, for the compounds of formula I where Q is methyl, tri-(lower-alkyl) orthoacetate, preferably where lower-alkyl is methyl or ethyl.

The reaction of an alkanoic acid or alkanoic anhydride with 2-PY-4,5,6-pyrimidinetriamine is carried out by heating the reactants at about 140° C. to 250° C., preferably at about 140° C. to 220° C., in the absence or presence of a suitable inert solvent, such as, an eutectic mixture of diphenyl and diphenyl ether. For example, use of acetic anhydride, propionic anhydride, isobutyric acid or trimethylacetic anhydride produces the compound of formula I where Q is methyl, ethyl, 1-methylethyl or 1,1-dimethylethyl, respectively.

The preparation of 8-methyl-2-PY-9H-purin-6-amine by reacting 2-PY-4,5,6-pyrimidinetriamine with a tri-(lower-alkyl)orthoacetate is conveniently and preferably carried out by heating the reactants at about 50° C. to 100° C., preferably about 60° C. to 80° C., in the absence or presence of a suitable solvent, e.g., a lower-alkanol, preferably ethanol; other solvents include dimethylformamide, p-dioxane, toluene, and the like. Similarily the preparation of 8-(methyl or ethyl)-2-PY-9H-purin-6-amine by reacting 2-PY-4,5,6-pyrimidinetriamine respectively with dimethylacetamide dimethyl acetal or with dimethylpropionamide dimethyl acetal is carried out by heating the reactants at about 50° C. to 100° C., preferably at about 60° C. to 80° C., in the absence or presence of a suitable solvent, e.g., dimethylformamide, acetonitrile, p-dioxane, and the like.

The intermediate 2-PY-4,5,6-pyrimidinetriamines (II) are prepared by the generally known procedure of first reacting a pyridinecarboxamidine of the formula, PY—C(=NH)NH₂, with α-phenylazomalononitrile to produce 5-phenylazo-2-PY-4,6-diaminopyrimidine and then catalytically hydrogenating the said 5-phenylazo compound to produce II.

The intermediate pyridinecarboxamidines are generally known compounds which are prepared by conventional means.

The preparation of 6-amino-2-PY-9H-purin-8-thiol (I, Q is SH) is carried out by reacting 2-PY-4,5,6-pyrimidinetriamine with an alkali metal xanthate, thiourea or thiocarbonyldiimidazole. The reaction using an alkali metal xanthate, preferably the sodium or potassium salt, is conveniently run by refluxing the reactants in a mixture of water and a lower-alkanol, preferably aqueous ethanol. The reaction using thiourea is conveniently run by heating the reactants in refluxing n-amyl alcohol or other suitable solvent inert under the reaction conditions. The reaction using thiocarbonyldiimidazole is conveniently run at room temperature or above (up to about 40° C. to 75° C.) in a suitable solvent, preferably dimethylformamide.

The preparation of 8-(ethylthio or methylthio)-2-PY-9H-purin-6-amine (I, Q is $C_2H_5S$ or $CH_3S$) is carried out by reacting 6-amino-2-PY-9H-purin-8-thiol, preferably as its alkali metal salt, with a lower-alkylating agent, preferably an ethyl or a methyl ester of a strong inorganic acid or an organic sulfonic acid. This reaction is conveniently run by mixing the reactants in a suitable solvent, e.g., aqueous ethanol, at room temperature or up to about 100° C. if necessary to facilitate the reaction.

The following examples will further illustrate the invention without, however, limiting it thereto.

A. 2-PY-4,5,6-PYRIMIDINETRIAMINES

A-1. 2-(4-Pyridinyl)-4,5,6-pyrimidinetriamine A mixture containing 146.5 g of 5-(phenylazo)-2-(4-pyridinyl)-4,6-pyrimidinediamine, 1200 ml of acetic acid and 4 g of 10% palladium-on-charcoal was shaken with hydrogen under catalytic hydrogenation conditions until there was an uptake of 1 mole of hydrogen, taking about 40 minutes and the reaction being exothermic. The reaction mixture was cooled and the catalyst filtered off. The filtrate was concentrated, the residue dissolved in 2 liters of hot water, and the solution filtered. The filtrate was made basic by adding ammonium hydroxide solution. The yellow crystalline solid that separated was collected, washed successively with water and ether, and dried in an oven at 95° C. to yield 82.5 g of 2-(4-pyridinyl)-4,5,6-pyrimidinetriamine, m.p. 230°-232° C.

In another run a mixture containing 35 g of 5-(phenylazo)-2-(4-pyridinyl)-4,6-pyrimidinediamine, 150 ml of dimethylformamide and 2.5 g of Raney nickel was shaken under catalytic hydrogenation conditions at 85°-90° C. for 12 hours until the hydrogen uptake stopped. The reaction mixture was cooled to room temperature, the catalyst was filtered off and the filtrate was evaporated to dryness. The residue was recrystallized from 6N hydrochloric acid, washed with ethanol and dried to yield 15.8 g of 2-(4-pyridinyl)-4,5,6-pyrimidinetriamine trihydrochloride, m.p.>320° C.

Other acid-addition salts of 2-(4-pyridinyl)-4,5,6-pyrimidinetriamine are conveniently prepared by adding to a mixture of 2 g of 2-(4-pyridinyl)-4,5,6-pyrimidinetriamine in about 40 ml of aqueous methanol the appropriate acid, e.g., concentrated sulfuric acid, concentrated phosphoric acid, to a pH of about 2 to 3, chilling the mixture after partial evaporation and collecting the precipitated salt, e.g., sulfate, phosphate, respectively. Also, the acid-addition salt is conveniently prepared in aqueous solution by adding to water with stirring molar equivalent quantities each of 2-(4-pyridinyl)-4,5,6-pyrimidinetriamine and the appropriate acid, e.g., lactic acid or hydrochoric acid, to prepare respectively the monolactate or monohydrochloride salt in aqueous solution.

The intermediate 5-(phenylazo)-2-(4-pyridinyl)-4,6-pyrimidinediamine was prepared as follows: a mixture containing 477 g of isonicotinamidine hydrochloride, 3 liters of ethanol and 170 g of sodium methoxide was stirred for 30 minutes and to the mixture was added 340 g of α-(phenylazo)malononitrile and the reaction mixture was stirred under reflux for 5 hours and then poured into 3 liters of water. The solid that separated was collected, washed with water and dried in a vacuum oven at 90°-95° C. to yield 356 g of 5-(phenylazo)-2-(4-pyridinyl)-4,6-pyrimidinediamine, m.p. 302°-305° C.

Following the procedure described in A-1 using in place of isonicotinamidine hydrochloride a molar equivalent quantity of the appropriate alkylated-isonicotinamidine, it is contemplated that the 2-PY-4,5,6-pyrimidinetriamines of Examples A-2 thru A-5 can be obtained.

A-2. 2-(2-Methyl-4-pyridinyl)-4,5,6-pyrimidinetriamine, using 2-methylisonicotinamidine.

A-3. 2-(3-Methyl-4-pyridinyl)-4,5,6-pyrimidinetriamine, using 3-methylisonicotinamidine.

A-4. 2-(2-Ethyl-4-pyridinyl)-4,5,6-pyrimidinetriamine, using 3-ethylisonicotinamidine.

A-5. 2-(2,6-Dimethyl-4-pyridinyl)-4,5,6-pyrimidinetriamine using 2,6-dimethylisonicotinamidine.

B. 8-Q-2-PY-9H-PURIN-6-AMINES

B-1. 8-Methyl-2-(4-pyridinyl)-9H-purin-6-amine A mixture containing 7 g of 2-(4-pyridinyl)-4,5,6-pyrimidinetriamine, 20 ml of triethyl orthoacetate, 75 ml of ethanol and 7 ml of triethylamine was stirred under reflux for 18 hours and evaporated to dryness. The residue was dissolved in ethanol, the solution was treated with decolorizing charcoal and filtered, and the filtrate was stripped to dryness in vacuo. The residue was taken up in 50 ml of dilute hydrochloric acid; the solution was allowed to stand at room temperature for 2 hours and was then made basic by adding ammonium hydroxide solution. The precipitated product was collected, dried in a vacuum oven at 90°-95° C. and recrystallized from isopropyl alcohol to yield 1.8 g. of 8-methyl-2-(4-pyridinyl)-9H-purin-6-amine, m.p.>300° C. Two additional runs of the above preparation were carried out and the resulting combined 4.2 g of product was combined with the above 1.8 g of product and the combined material was dissolved in 6N hydrochloric acid and the mixture was evaporated to dryness in vacuo. The residue was refluxed with ethanol, the hot mixture filtered, and the product that separated was collected and dried to yield 6.1 g of 8-methyl-2-(4-pyridinyl)-9H-purin-6-amine as its dihydrochloride, m.p.>330° C.

B-2. 8-Methyl-2-(4-pyridinyl)-9H-purin-6-amine A mixture containing 49 g of 2-(4-pyridinyl)-4,5,6-pyrimidinetriamine and 500 ml of acetic anhydride was refluxed for 24 hours and then stripped to dryness. The residue was suspended in water and basified with ammonium hydroxide solution. The resulting mixture was cooled and the product was collected. The product was suspended in 500 ml of ethanol and to the suspension was added 100 ml of 35% aqueous sodium hydroxide solution and the mixture was refluxed for 3 hours. The resulting solution was treated with decolorizing charcoal and filtered. The filtrate was evaporated to dryness in vacuo and the remaining residue was suspended in 700 ml of water, the suspension was acidified with acetic acid and then basified with ammonium hydroxide solution. The resulting mixture was cooled; the resulting precipitate was collected and dissolved in 2 liters of boiling ethanol. The ethanolic solution was treated with decolorizing charcoal and filtered. The filtrate was heated to reflux to effect dissolution and to it was added cautiously 50 ml of concentrated hydrochloric acid. The resulting mixture was cooled in ice and the product that separated was collected, washed with ethanol, dried in vacuo at 70° C. to yield 49 g of 8-methyl-2-(4-pyridinyl)-9H-purin-6-amine as its dihydrochloride, m.p.>310° C.

Other acid-addition salts of 8-methyl-2-(4-pyridinyl)-9H-purin-6-amine are conveniently prepared by adding to a mixture of 2 g of 8-methyl-2-(4-pyridinyl)-9H-purin-6-amine in about 40 ml of aqueous methanol the appropriate acid, e.g., concentrated sulfuric acid, concentrated phosphoric acid, to a pH of about 2 to 3, chilling the mixture after partial evaporation and collecting the precipitated salt, e.g., sulfate, phosphate, respectively. Also, the acid-addition salt is conveniently prepared in aqueous solution by adding to water with stirring molar equivalent quantities each of 8-methyl-2-(4-pyridinyl)-9H-purin-6-amine and the appropriate acid, e.g., lactic acid or hydrochloric acid, to prepare respectively the monolactate or monohydrochloride salt in aqueous solution.

B-3. 8-Ethyl-2-(4-pyridinyl)-9H-purin-6-amine—A mixture containing 10.5 g of 2-(4-pyridinyl)-4,5,6-pyrimidinetriamine and 15 ml of propionic anhydride was heated at 170°-180° C. for 30 minutes, cooled, and poured in iced cold water. The aqueous mixture was made basic by adding ammonium hydroxide solution. The product was extracted from the alkaline mixture using chloroform and the chloroform extract was evaporated to dryness. The residue, which consisted predominantly of N-propionyl-8-ethyl-2-(4pyridinyl)-9H-purin-6-amine, was refluxed for 1 hour with a mixture of 100 ml of methanol and 25 ml of 35% aqueous sodium hydroxide solution and then cooled. The methanol was distilled off in vacuo and the remaining material was acidified with acetic acid. The separated solid was collected, recrystallized from isopropyl alcohol and dried at 80°-85° C. to yield 8.5 g of 8-ethyl-2-(4-pyridinyl)-9H-purin-6-amine, m.p.>300° C.

B-4. 8-(1-Methylethyl)-2-(4-pyridinyl)-9H-purin-6-amine—A mixture containing 15 g of 2-(4-pyridinyl)-4,5,6-pyrimidinetriamine and 20 ml of isobutric acid was heated at 200°-220° C. for 1 hour. Since the reaction-mixture solidified and did not form a melt, 30 ml of an eutectic mixture of diphenyl and diphenyl ether was added and the mixture heated at 210°-220° C. for 1 hour and cooled. The reaction mixture was filtered and the filtrate was concentrated in vacuo. The resulting residue was recrystallized once from isopropyl alcohol and a second time from isopropyl alcohol and ether to produce 5.3 g of 8-(1-methylethyl)-2-(4-pyridinyl)-9H-purin-6-amine, m.p. 269°-272° C. This product was converted into its dimethanesulfonate salt by treating a solution of it in ethanol with excess methanesulfonic acid, collecting the salt and drying it at 90°-95° C. to obtain 8.3 g of 8-(1-methylethyl-2-(4-pyridinyl)-9H-purin-6-amine as its dimethanesulfonate, m.p. 248°-251° C.

B-5. 8-(1-Methylethyl)-2-(4-pyridinyl)-9H-purin-6-amine—A mixture containing 38 g of 2-(4-pyridinyl)-4,5,6-pyrimidinetriamine, 50 ml of isobutyric acid and 125 ml of an eutetic mixture of diphenyl and diphenyl ether was heated to reflux (165° C.) for 1 hour; the reaction mixture was concentrated until the internal temperature to 215° C.; and, the remaining reaction mixture was heated at 250° C. for 1 hour. The reaction mixture was then diluted with 350 ml of ether, the mixture shaken well, and the separated solid was collected and washed with ether. The solid was recrystallized from ethanol using decolorizing charcoal to yield 8.0 g of 8-(1-methylethyl)-2-(4-pyridinyl)-9H-purin-6-amine.

This portion of product was combined with another 13.0 g of product obtained by another run starting with 38 g of 2-(4-pyridinyl)-4,5,6-pyrimidinediamine, 125 ml of an eutectic mixture of diphenyl and diphenyl ether and 50 ml of isobutyric acid, and the resulting 21 g of product was slurried in ethanol and the mixture made acidic with ethanolic hydrogen chloride. After a precipitate appeared, the mixture was cooled. The resulting precipitate was collected, washed successively with cold ethanol and cold ether, and dried at 60° C. in vacuo to yield 22.0 g of recrystallized product. This material was dissolved in boiling ethanol with enough water added to complete dissolution and the hot solution was cooled. The separated product was collected, washed successively with ethanol and ether, and dried in vacuo at 60° C. to yield 17.5 g of 8-(1-methylethyl)-2-(4-pyridinyl)-9H-purin-6-amine as its dihydrochloride hemihydrate m.p.>300° C.

Other acid-addition salts of 6-(1-methylethyl)-2-(4-pyridinyl)-9H-purin-6-amine are conveniently prepared by adding to a mixture of 2 g of 6-(1-methylethyl)-2-(4-pyridinyl)-9H-purin-6-amine in about 40 ml of aqueous methanol the appropriate acid, e.g., concentrated sulfuric acid, concentrated phosphoric acid, to a pH of about 2 to 3, chilling the mixture after partial evaporation and collecting the precipitated salt, e.g., sulfate, phosphate, respectively. Also, the acid-addition salt is conveniently prepared in aqueous solution by adding to water with stirring molar equivalent quantities each of 6-(1-methylethyl)-2-(4-pyridinyl)-9H-purin-6-amine and the appropriate acid, e.g., lactic acid or hydrochloric acid, to prepare respectively the monolactate or monohydrochloride salt in aqueous solution.

B-6. 8-(1,1-Dimethylethyl)-2-(4-pyridinyl)-9H-purin-6-amine—A mixture containing 20.2 g of 2-(4-pyridinyl)-4,5,6-pyrimidinetriamine and 25 ml of trimethylacetic anhydride was refluxed for 2 hours at 180°-190° C. and then cooled to room temperature. The cooled reaction mixture was slurried in water and the separated solid was collected, washed with ether, recrystallized once from ethanol-ether and once from isopropyl alcohol using decolorizing charcoal, washing with ether and drying at 90°-95° C. to produce 7.1 g of 8-(1,1-dimethylethyl)-2-(4-pyridinyl)-9H-purin-6-amine as its monohydrate, m.p. 272°-274° C.

Acid-addition salts of 8-(1,1-dimethylethyl)-2-(4-pyridinyl)-9H-purin-6-amine are conveniently prepared by adding to a mixture of 2 g of 8-(1,1-dimethylethyl)-2-(4-pyridinyl)-9H-purin-6-amine in about 40 ml of aqueous methanol the appropriate acid, e.g., concentrated sulfuric acid, concentrated phosphoric acid, to a pH of about 2 to 3, chilling the mixture after partial evaporation and collecting the precipitated salt, e.g., sulfate, phosphate, respectively. Also, the acid-addition salt is conveniently prepared in aqueous solution by adding to water with stirring molar equivalent quantities each of 8-(1,1-dimethylethyl)-2-(4-pyridinyl)-9H-purin-6-amine and the appropriate acid, e.g., lactic acid or hydrochloric acid, to prepare respectively the monolactate or monohydrochloride salt in aqueous solution.

B-7. 6-Amino-2-(4-pyridinyl)-9H-purin-8-thiol—A mixture containing 10.1 g of 2-(4-pyridinyl)-4,5,6-pyrimidinetriamine, 22.8 g of thiourea and 100 ml of n-amyl alcohol was refluxed with stirring for 48 hours and then evaporated to dryness on a rotary evaporator. To the residue was added 100 ml of 35% aqueous sodium hydroxide solution and 50 ml of water. The resulting mixture was heated on a steam bath for 1 hour, treated with decolorizing charcoal and filtered. The filtrate was acidified with acetic acid whereupon there resulted a yellow gel, which was heated with stirring on a hot plate for 1 hour until the gel changed into fine solid particles. The solid was collected, washed with water and dried, and then digested with ethanol, collected and dried at 90°–95° C. to yield 4.8 g of 6-amino-2-(4-pyridinyl)-9H-purin-8-thiol, m.p.>330° C. This compound was dissolved in ethanol and treated with an excess of methanesulfonic acid and the separated salt was collected and dried to yield 5.6 g of 6-amino-2-(4-pyridinyl)-9H-purin-8-thiol as its methanesulfonate, m.p.>330° C.

B-8. 8-Ethylthio-2-(4-pyridinyl)-9H-purin-6-amine—A mixture containing 12.2 g of 6-amino-2-(4-pyridinyl)-9H-purin-8-thiol, 100 ml of dimethylformamide and 14.2 g of anhydrous potassium carbonate was heated with stirring on a steam bath for 30 minutes and then cooled. To the stirred mixture was added 4.2 ml of ethyl iodide. The resulting reaction mixture was stirred for 3 hours at ambient temperature and then poured into ice cold water. The separated solid was collected, washed with water, air-dried and recrystallized from ethanol to produce 7.9 g of product. The mother liquor was evaporated to dryness in vacuo and the residue combined with said product and the combined material was dissolved in isopropyl alcohol, treated with an excess of methanesulfonic acid and the resulting precipitate was collected and dried at 80°–85° C. to yield 11.6 g of 8-ethylthio-2-(4-pyridinyl)-9H-purin-6-amine as its dimethanesulfonate salt, m.p. 168°–170° C. with decomposition.

Other acid-addition salts of 8-ethylthio-2-(4-pyridinyl)-9H-6amine are conveniently prepared by adding to a mixture of 2 g of 8-ethylthio-2-(4-pyridinyl)-9H-6-amine in about 40 ml of aqueous methanol the appropriate acid, e.g., concentrated sulfuric acid, concentrated phosphoric acid, to a pH of about 2 to 3, chilling the mixture after partial evaporation and collecting the precipitated salt, e.g., sulfate, phosphate, respectively. Also, the acid-addition salt is conveniently prepared in aqueous solution by adding to water with stirring molar equivalent quantities each of 8-ethylthio-2-(4-pyridinyl)-9H-6-amine and the appropriate acid, e.g., lactic acid or hydrochloric acid, to prepare respectively the monolactate or monohydrochloride salt in aqueous solution.

B-9. 8-Methylthio-2-(4-pyridinyl)-9H-purin-6-amine can be prepared following the procedure described in Example B-8 using in place of ethyl iodide a molar equivalent quantity of methyl iodide.

Following the procedure described in Example B-5 using in place of 2-(4-pyridinyl)-4,5,6-pyrimidinetriamine a molar equivalent quantity of the appropriate 2-PY-4,5,6-pyrimidinetriamine, it is contemplated that the corresponding 8-(1-methylethyl)-2-PY-9H-purin-6-amines of Examples B-10 thru B-13 can be obtained.

B-10. 8-(1-methylethyl)-2-(2-methyl-4-pyridinyl)-9H-purin-6-amine, using 2-(2-methyl-4-pyridinyl)-4,5,6-pyrimidinetriamine.

B-11. 8-(1-Methylethyl)-2-(3-methyl-4-pyridinyl)-9H-purin-6-amine, using 2-(3-methyl-4-pyridinyl)-4,5,6-pyrimidinetriamine.

B-12. 8-(1-Methylethyl)-2-(2-ethyl-4-pyridinyl)-9H-purin-6-amine, using 2-(2-ethyl-4-pyridinyl)-4,5,6-pyrimidinetriamine.

B-13. 8-(1-Methylethyl)-2-(2,6-dimethyl-4-pyridinyl)-9H-purin-6-amine, using 2-(2,6-dimethyl-4-pyridinyl)-4,5,6-pyrimidinetriamine.

The usefulness of compounds of formula I or salts thereof as cardiotonic agent is demonstrated by their effectiveness in standard pharmacological test procedures, for example, in causing a significant increase in contractile force of the isolated cat atria and papillary muscle and/or in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1980.

When tested by said isolated cat atria and papillary muscle procedure, compounds of formula I or pharmaceutically acceptable acid-addition salts thereof at doses of 30, 100 and/or 300 µg/ml., were found to cause significant increases, that is, greater than 25% in papillary muscle force and significant increases, that is, greater than 25%, in right atrial force, while causing a lower percentage increase (preferably about one-half or less than the percentage increase in right atrial force or papillary muscle force) in right atrial rate. For example, when tested at said dose levels by this procedure, the compounds of Examples B-2, B-3, B-5, B-6 and B-8 were found to cause increases of 32 to 122% in papillary muscle force and/or right atrial force.

When tested by said anesthetized dog procedure, the compounds of formula I or pharmaceutically acceptable acid-addition salts thereof at doses of 1.0, 3.0 and/or 10 mg/kg administered intravenously were found to cause significant increases, that is, 25% or greater, in cardiac contractile force or cardiac contractility with lower changes in heart rate and blood pressure. For example, when tested at one or more of said dose levels by this procedure, the compounds of Examples B-5, B-6 and B-8 were found to cause increases of 26 to 132% in contractile force and lower changes in heart rate and blood pressure.

The present invention includes within its scope a cardiotonic composition for increasing cardiac contractility, said composition comprising a pharmaceutically acceptable carrier and, as the active component thereof, a cardiotonically effective amount of the compound of formula I where Q is methyl, ethyl, 1-methylethyl, 1,2-dimethylethyl, methylthio or ethylthio or pharmaceutically acceptable acid-addition salt thereof. The invention also includes within its scope the method for increasing cardiac contractility in a patient requiring such treatment which comprises administering to such patient a cardiotonically effective amount of said compound of formula I or pharmaceutically acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions can also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions can also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilising, preserving, wetting, emulsifying and dispersing agents.

They can be sterilized, for example, by filtration through a bacteria-retaining filter, by incorporation of sterilising agents in the compositions, by irradiation or by heating. They can also be manufactured in the form of sterile solid compositions which can be dissolved in sterile water or some other sterile injectable medium immediately before use.

The percentages of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:
1. 8-Q-2-PY-9H-purin-6-amine having the formula

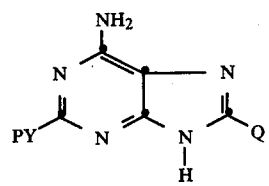

where Q is methyl, ethyl, 1-methylethyl, 1,1-dimethylethyl, mercapto, methylthio or ethylthio, and Py is 4-pyridinyl or 4-pyridinyl having one or two lower-alkyl substituents, or acid-addition salt thereof.

2. A compound according to claim 1 where Py is 4-pyridinyl, and Q is 1-methylethyl, methyl or ethylthio.

3. 8-(1-Methylethyl)-2-(4-pyridinyl)-9H-purin-6-amine according to claim 1.

4. 8-Methyl-2-(4-pyridinyl)-9H-purin-6-amine according to claim 1.

5. 8-Ethylthio-2-(4-pyridinyl)-9H-purin-6-amine according to claim 1.

6. A cardiotonic composition for increasing cardiac contractility, said composition comprising a pharmaceutically acceptable inert carrier and, as the active component thereof, a cardiotonically effective amount of the 8-Q-2-PY-9H-purin-6-amine of claim 1 or pharmaceutically acceptable acid-addition salt thereof, where PY is 4-pyridinyl or 4-pyridinyl having one or two lower-alkyl substituents, and Q is methyl, ethyl, 1-methylethyl, 1,1-dimethylethyl, methylthio or ethylthio.

7. A composition according to claim 6 where PY is 4-pyridinyl and Q is 1-methylethyl, methyl or ethylthio.

8. The method for increasing cardiac contractility in a patient requiring such treatment which comprises administering to such patient a cardiotonically effective amount of the composition of claim 6.

* * * * *